US011386985B2

(12) United States Patent
Witchey

(10) Patent No.: US 11,386,985 B2
(45) Date of Patent: Jul. 12, 2022

(54) HEALTHCARE TRANSACTION VALIDATION VIA BLOCKCHAIN SYSTEMS AND METHODS

(71) Applicant: Nant Holdings IP, LLC, Culver City, CA (US)

(72) Inventor: Nicholas J. Witchey, Laguna Hills, CA (US)

(73) Assignee: NANT HOLDINGS IP, LLC, Culver City, CA (US)

( * ) Notice: Subject to any disclaimer, the term of this patent is extended or adjusted under 35 U.S.C. 154(b) by 610 days.

(21) Appl. No.: 16/410,655

(22) Filed: May 13, 2019

(65) Prior Publication Data

US 2019/0267119 A1    Aug. 29, 2019

Related U.S. Application Data

(62) Division of application No. 14/711,740, filed on May 13, 2015, now Pat. No. 10,340,038.

(Continued)

(51) Int. Cl.
| | |
|---|---|
| *G16H 10/60* | (2018.01) |
| *G06Q 30/00* | (2012.01) |
| *G06F 21/00* | (2013.01) |
| *G06F 21/64* | (2013.01) |
| *H04W 12/02* | (2009.01) |

(52) U.S. Cl.
CPC ............ *G16H 10/60* (2018.01); *G06F 21/00* (2013.01); *G06F 21/645* (2013.01); *G06Q 30/018* (2013.01); *H04W 12/02* (2013.01); *G06Q 2250/30* (2013.01)

(58) Field of Classification Search
None
See application file for complete search history.

(56) References Cited

U.S. PATENT DOCUMENTS 7,356,696 B1    4/2008  Jakobsson et al.
7,600,255 B1   10/2009  Baugher
(Continued)

FOREIGN PATENT DOCUMENTS

CN            103927659 A     7/2014

OTHER PUBLICATIONS

Amirtha, "Meet Ether, The Bitcoin-Like Cryptocurrency That Could Power The Internet Of Things," Business Technology Thought Leadership, May 21, 2015, Fast Company.

(Continued)

*Primary Examiner* — Steven S Kim
*Assistant Examiner* — Jason B Fenstermacher
(74) *Attorney, Agent, or Firm* — Mauriel Kapouytian Woods LLP; Elaine K. Lee; Andrew A. Noble

(57) ABSTRACT

Healthcare transaction validation systems and methods are presented. Healthcare transactions associated with a stakeholder are compiled into a chain of healthcare transaction blocks. The chain can be considered a chronicle of person's healthcare path through life. When a transaction is conducted, the corresponding healthcare parameters (e.g., inputs, outputs, clinical evidence, outcomes, etc.) are sent to one or more validation devices. The devices establish a validity of the transaction and generate a new block via a proof-of-work principle. Once the new block has been calculated it can be appended to the stakeholder's health care blockchain.

21 Claims, 4 Drawing Sheets

Related U.S. Application Data

(60) Provisional application No. 61/992,734, filed on May 13, 2014.

(56) References Cited

U.S. PATENT DOCUMENTS

| | | | |
|---|---|---|---|
| 8,412,952 | B1 | 4/2013 | Ramzan et al. |
| 8,615,532 | B2 | 12/2013 | Bessette |
| 9,014,661 | B2 | 4/2015 | deCharms |
| 10,340,038 | B2 | 7/2019 | Witchey |
| 11,270,298 | B2 | 3/2022 | Pauker et al. |
| 2007/0055552 | A1 | 3/2007 | St. Clair et al. |
| 2008/0208996 | A1* | 8/2008 | Thompson .......... H04L 67/1065 709/206 |
| 2009/0076855 | A1 | 3/2009 | McCord |
| 2009/0144200 | A1 | 6/2009 | Yoshioka |
| 2013/0290022 | A1* | 10/2013 | Shah ................ G06Q 10/101 705/3 |
| 2014/0344015 | A1* | 11/2014 | Puertolas-Montanes .................. G06Q 30/0217 705/7.29 |
| 2014/0372140 | A1* | 12/2014 | Reddy ................. G06F 8/30 705/2 |
| 2015/0205929 | A1* | 7/2015 | Brama ................ G16H 40/67 705/3 |
| 2015/0220928 | A1* | 8/2015 | Allen ................ G06Q 20/3829 705/67 |
| 2015/0244690 | A1* | 8/2015 | Mossbarger .......... H04L 9/3263 713/171 |

OTHER PUBLICATIONS

Assia et al., "Colored Coins—BitcoinX," White Paper, Coloredcoins.org.
Back, "Enabling Blockchain Innovations with Pegged Sidechains," White Paper, Oct. 22, 2014, Blockstream.com.
Biggs, "Your Next Passport Could Be on the Blockchain," Oct. 31, 2014, Techcrunch.com.
Bradbury, "How the Blockchain Could Stop Firms Cooking the Books," CoinDesk, Feb. 7, 2015, Coindesk.com.
Cawrey, "Neuroware Launches 'Future-Proof' API for Cryptocurrency Apps," CoinDesk, Jan. 10, 2015, coindesk.com.
Chavez-Dreyfuss, "Exclusive: IBM Looking at Adopting Bitcoin Technology for Major Currencies," Business and Financial News, Mar. 12, 2015, Reuters.
Davarpanah et al., "NeuCoin: the First Secure, Cost-Efficient and Decentralized Cryptocurrency," White Paper, Mar. 25, 2015, NeuCoin.
Deane, "Students Aim to Enhance Crypto-Currency Transparency," Feb. 3, 2015, Technology/Computer Sciences, Phys.org.
U.S. Federal Reserve System, "Strategies for Improving the U.S. Payment System," Strategy Report, Jan. 26, 2015, Fedpaymentsimprovement.org.
Gillespie, "Alternative Cryptocurrency Claims to Have Won the Race to Smart Contracts," Blockchain Agenda, Jan. 23, 2015, Insidebitcoins.com, MecklerMedia.
Higgins, "Factom Outlines Record-Keeping Network That Utilises Bitcoin's Blockchain," Nov. 19, 2014, Coindesk.com.
Higgins, "IBM Reveals Proof of Concept for Blockchain-Powered Internet of Things," Jan. 17, 2015, Coindesk.com.
King et al., "PPCoin: Peer-to-Peer Crypto-Currency with Proof-of-Stake," Thesis, Aug. 19, 2012, Peercoin.net.
Miers et al., "Zerocoin: Anonymous Distributed E-Cash from Bitcoin," 2013 IEEE Symposium on Security and Privacy, May 19, 2013, pp. 397-411.
Morgan, "Using Blockchain Technology to Prove Existence of a Document," Empowered Law, Jun. 21, 2014, WordPress.com.
Nakamoto, "Bitcoin: A Peer-to-Peer Electronic Cash System," White Paper, Oct. 31, 2008.
"Executive Summary," NeuCon—Wiki, Feb. 3, 2015, NeuCoin.org.
Panikkar et al., "Adept: An IoT Practitioner Perspective—Draft Copy for Advance Review," IBM, 2015, CoinDesk.
Rosenfeld, "Overview of Colored Coins," White Paper, Dec. 4, 2012.
Shieber, "BlockCypher Raises Seed Funding To Be The Web Services For Cryptocurrency," TechCrunch, Jan. 14, 2015, WordPress.com.
Shieber, "Colu Aims To Bring Blockchain Technology Everywhere," TechCrunch, Jan. 27, 2015, WordPress.com.
Snow et al., "Factom—Business Processes Secured by Immutable Audit Trails on the Blockchain," White Paper Version 1.0, Nov. 17, 2014, Factom.org.
Torpey, K., "Permanent Record of 'The Age of Cryptocurrency' Entered into the Blockchain," Blockchain Agenda, Feb. 6, 2015, Insidebitcoins.com, MecklerMedia.
International Search Report and Written Opinion issued in International Application No. PCT/US2015/030665, dated Aug. 12, 2015, 11 pages.

\* cited by examiner

HEALTHCARE TRANSACTION VALIDATION VIA BLOCKCHAIN SYSTEMS AND METHODS

CROSS REFERENCE TO RELATED APPLICATIONS

This application is a divisional of U.S. Non-provisional application Ser. No. 14/711,740, filed May 13, 2015 which claims the benefit of U.S. Provisional Application No. 61/992,734, filed May 13, 2014. The entire content of that application is hereby incorporated herein by reference.

FIELD OF THE INVENTION

The field of the invention is transaction validation technologies.

BACKGROUND

The background description includes information that may be useful in understanding the present invention. It is not an admission that any of the information provided herein is prior art or relevant to the presently claimed invention, or that any publication specifically or implicitly referenced is prior art.

Cryptocurrencies have risen over the last few years. The most famous cryptocurrency is Bitcoin, launched in 2009, as described in the original paper openly published on May 24, 2009, by Nakamoto and titled "Bitcoin: A Peer-to-Peer Electronic Cash System" (see URL en.bitcoin.it/wiki/Bitcoin_white_paper).

Cryptocurrencies operate on the principle of applying proof-of-work (POW) principles to process Bitcoin transactions that are bound together in large blocks of data. The device that successfully meets the proof-of-work requirements (i.e., generating a double hash value with a required number of leading zero bits) for the transaction block and has their block accepted by peers receives a reward in the form of Bitcoins.

Although Bitcoin is probably the most famous application of POW, many others have applied POW to other areas of technology. For example, U.S. Pat. No. 7,356,696 to Jakobsson et al. titled "Proofs of Work and Bread Pudding Protocols", filed Aug. 1, 2000, describes re-using stale computations of a POW to continue minting digital currency.

Another example of using POW further afield from cryptocurrency includes U.S. Pat. No. 7,600,255 to Baugher titled "Preventing Network Denial of Service Attacks Using an Accumulated Proof-of-work Approach", filed Apr. 14, 2004. Baugher requires a computer client to generate a POW to access a service where the POW could include hashing a message until a desired number of leading bit-level zeros is found, similar to the POW of Bitcoin.

In a somewhat similar vein to Baugher, U.S. Pat. No. 8,412,952 to Ramzan et al. titled "Systems and Methods for Authenticating Requests from a Client Running Trialware Through a Proof of Work Protocol", filed May 6, 2009, also uses POW to grant access to services. Ramzan describes generating a cryptographic puzzle if no authentication token is included with a service request to run trialware. The client making the request must solve the cryptographic puzzle in order to receive authentication to proceed with running the trialware.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY

Interestingly, the above known proof-of-work (POW) systems have only focused on transaction processing or authentication. It has yet to be appreciated that POW systems could be deployed in other areas. One market that is fraught with issues includes healthcare systems that manage large volumes of electronic medical records (EMR). Example issues include enforcing privacy, standards compliance, interoperability, data format conversion, ensuring proper treatment applied to a patient, and especially the difficulty maintaining a continuity of treatment records for individuals. As a representative example of the state of the art, consider U.S. Pat. No. 8,615,532 to Bessette titled "System and Method for Electronically Managing Medical Data Files", filed Sep. 12, 2012. Bessette discusses one of myriad possible ways in which medical records can be updated assuming proper authentication.

Even with the countless healthcare management or EMR systems available, the systems lack the ability to properly construct a history of health transaction across various entities. A more ideal system would create of chain of transactions from various entities where each transaction is validated via a POW approach. Such a validation approach ensures that all entities are held responsible for their transactions by peer review while also preserving a record of healthcare transactions. Thus, there remains a need validating healthcare transactions.

The inventive subject matter provides apparatus, systems and methods in which a proof-of-work system can be employed to track or validate healthcare transactions. One aspect of the inventive subject matter includes a method of validating healthcare transactions. The disclosed methods can include receiving, by one or more validation devices, a healthcare transaction that includes a set of healthcare tokens that represent healthcare actions taken with respect to a stakeholder. For example, the healthcare tokens might include test results for a patient and a corresponding diagnosis from a doctor. The validation device continues executing the method by obtaining a historical block identifier of the stakeholder's healthcare historical blockchain. The healthcare historical blockchain represents a chronicle of healthcare activities in the form of a substantially linear set of healthcare transactions for the particular stakeholder (e.g., patient, doctor, insurance company, hospital, etc.). The method also includes receiving a validity requirement with respect to the healthcare actions indicating criteria that must be met in order for the system to accept a validation event with respect to the transaction. The validation device continues to validate the healthcare actions by obtain a digital signature of a validator, perhaps another healthcare provider's public key or an expert system identifier. In addition, the method includes obtaining a validity token indicating the validity of the healthcare actions (e.g., valid action, invalid action, indeterminate, etc.). Once the various pieces of information has been collected, the validation device calculates a validity block based on the transaction and according the validity requirements as a function of the healthcare action parameters: the validity token, historical block identifier, the set of healthcare tokens, and the digital signature. Should the validity requirements be met, the validation device can cause the healthcare historical blockchain to be updated, possibly by appending the validity block to the chain. In some embodiments, proof-of-work methods are not necessarily employed. In some embodiments, proof-of-stake methods are used to authenticate a validity block to be appended to a stakeholder's healthcare historical blockchain.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
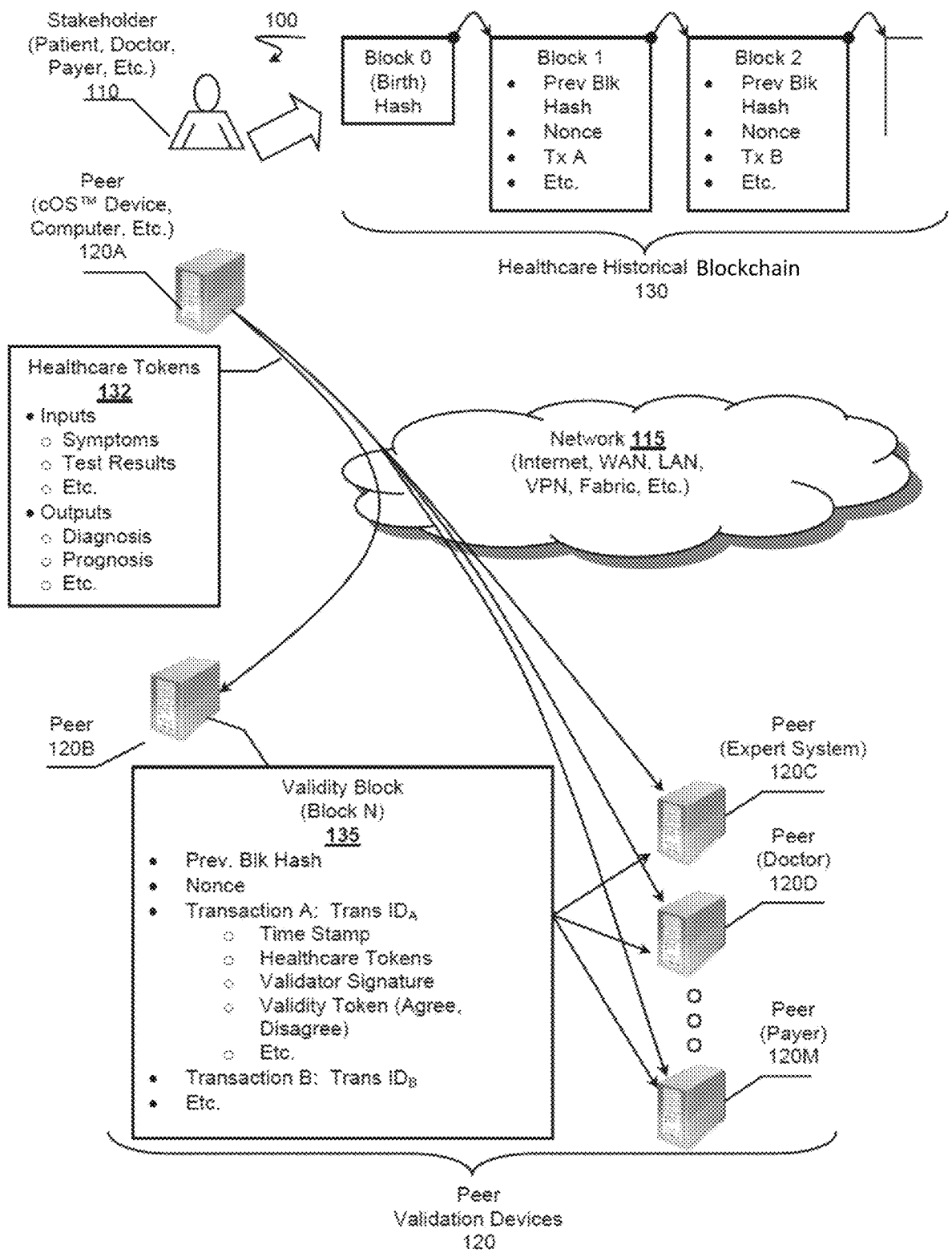
FIG. 1 is a schematic overview of a healthcare transaction ecosystem.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to be operable to provide the roles, responsibilities, or other functionality as discussed below with respect to the disclosed apparatus. Further, the disclosed technologies can be embodied as a computer program product that comprises a non-transitory computer readable medium storing the software instructions that causes a processor to execute the disclosed steps. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including construction and storage of a healthcare blockchain representing healthcare transactions of a patient or other healthcare stakeholder. Construction and storage of the healthcare blockchain enables computing devices to quickly and efficient validate or access healthcare data, thereby improving the performance of the computing devices.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The following discussion presents the inventive subject matter from the perspective of a patient interacting with a doctor. With respect to the disclosed subject matter, the patient's healthcare interactions are chronicled via an associated healthcare historical record represented by a blockchain. As the doctor performs services for the patient, information related to the services (e.g., inputs, outputs, codes, etc.) are packaged in the form of a healthcare transaction. The transactions are analyzed by peers in the ecosystem with respect to validity of the services. Once analyzed the transactions are incorporated into the patient's healthcare historical blockchain. Although the subject matter is presented from the perspective of a patient-doctor interaction, it should be appreciated that the transactions can relate to other types of interactions. Additional interactions could include doctor-insurance transactions, consumer-insurance interactions, patient-psychologist interactions, or other types of transactions.

FIG. 1 presents an overview of healthcare transaction validation system 100 where peers in a healthcare network are configured or programmed to manage healthcare transactions in the form of healthcare historical blockchains 130. Each block in the chain includes one or more healthcare transactions that further incorporate validation information representing the validity of the transaction as assessed by peer validation devices 120 (e.g., peers 120A through 120N), collectively referred to as peers 120. In some embodiments, peers 120 operate collectively in a peer-to-peer network. Further the device can exist within a clinical operating system ecosystem; possibly based on the cOS™ services offered by Nanthealth, LLC (see URL nanthealth.com/cos-clinical-operating-system).

Stakeholder 110 represents an entity that has a stake in a healthcare management lifecycle. A shown, stakeholder 110 could be a patient. However, stakeholder 110 could represent other types of entities. In some embodiments, stakeholder 110 could be another person, possibly a doctor, a nurse, a technician, a care provider, a guardian, a parent, a broker, or other individual. Further, stakeholder 110 could also include other types of entities including a company, an affiliation, a hospital, an organization, a demographic, a community, or other type of entity.

Of particular interest with respect to the inventive subject matter is that each stakeholder 110 could have associated healthcare historical blockchain (HHBC) 130. HHBC 130 represents a chronicle or ledger (e.g., public ledger, private ledger, protected ledger, etc.) of healthcare transactions for stakeholder 110. With respect to a patient, HHBC 130 might start with an initial block or genesis block created at birth that includes information associated with the patient's birth (e.g., parent information, attending physician, Apgar score, etc.). Each subsequent healthcare transaction for the patient can be combined with HHBC 130 as a new block, possibly until the HHBC becomes terminated at the death of the patient. It should be appreciated that each entity can have its own blockchain in the disclosed ecosystem rather than the complete ecosystem having a single chain covering all transactions as is done with cryptocurrencies.

HHBC 130 could comprise any number of blocks. For a healthy patient, HHBC 130 might only increase in size by one block per year based on annual visits to the doctor. However, when stakeholder 110 comprises a surgeon, the surgeon's HHBC 130 might represent performed surgeries where the surgeon's HHBC might increase in size by several blocks per day. Even further, when stakeholder 110 is a hospital, HHBC 130 could increase by hundreds of blocks per day. Large scale insurance companies might have HHBCs 130 that increase by thousands of blocks per day.

Returning to the example shown where a patient interacts with a doctor; the doctor works to understand the circumstances of the patient. Such information can be considered to represent input information related to the healthcare transaction in progress. Based on the information, the doctor preforms one or more actions; possibly including applying treatment, generating a diagnosis, establishing a prognosis, or other types of actions. The actions taken by the doctor can be considered outputs to or outcomes of the healthcare transaction.

The various attributes or properties of the inputs and outputs can be represented by healthcare tokens 132. Healthcare tokens 132 represent the information defining the nature of the healthcare transaction associated within stakeholder 110. In more preferred embodiments, healthcare tokens 132 adhere to a defined, possibly standardized, healthcare namespace. For example, the healthcare namespace might include standardized codes (e.g., ICD 9, ICD 10, CPT, DSM, etc.) that categorize the inputs and outputs.

Use of a common healthcare namespace aids in creating a common reference frame or nomenclature among peers 120 as they process or validate the healthcare transactions. Such an approach ensures all peers 120 or stakeholders 110 represent information according to a common language, which ensures that the transactions are processed in a uniform, repeatable, and verifiable manner. More preferred healthcare namespaces include normalized terms, especially in circumstances where conflicting codes might exist (e.g., ICD-9 codes 290-319 for mental disorders versus DSM-IV codes for mental disorder; although some harmonization exists between these two schemes).

Peer 120A, perhaps the doctor's EMR system, can package healthcare tokens 132 for delivery to one or more validation devices; peers 120B through 120M for example. For example, healthcare tokens 132 can be packaged in an XML, JSON, or other formats suitable for exchanging data over network 115. The phrase "tokens" herein is used in the broader sense of parsing data into tokens (useful groupings of data) rather than in the narrow data security context. In other words, healthcare tokens and validity tokens referenced herein are not necessarily hashed or otherwise processed to make the underlying data unrecoverable.

In the example shown, peer 120B obtains healthcare tokens 132 and attempts generate validity block 135 that comprises the healthcare transaction represented by healthcare tokens 132 among other pieces of information. For example, the transaction could include a transaction ID, a time stamp, validator digital signature, or other data. Of especial interest, the transaction validity block 135 also incorporates a validity token that represents the validator's perspective on the validity of the interaction between the patient and the doctor. The validity token could include simple information such as "agree" or "disagree". A more complex validity token could include alternative information such as suggestions or recommendations on improving the transaction; perhaps an alternative diagnosis for example.

Peer 120B generates validity block 135 according to validity requirement. It should be appreciated that the other peers can, at the same time, also process the same transaction. The validity requirement can be considered a proof-of-work requirement related to the healthcare transactions. Further, the validity requirement can incorporate other criteria that should be satisfied before the transactions are considered properly processed.

Peer 120B builds validity block 135 from one or more transactions as shown. For a single patient visiting a doctor office, validity block 135 will likely have only a single transaction. For a more active stakeholder 110 (e.g., a hospital, etc.), validity block 135 could comprise multiple transactions.

Validity block 135 is processed by combining previous block information (e.g., a hash of a block header) from HHBC 130 with additional information, thereby linking validity block 135 with the blockchain. As discussed previously, the additional transaction information can include time stamp, healthcare tokens 132, validator digital signature, and especially the validity token. Peer 120B can re-calculate a value for validity block 135, typically a hash of the validity block's header along with hash information from the transactions, until the resulting value satisfies the validity requirement. For example, in embodiments where validity block 135 is processed via a hash function (e.g., SHA256, Scrypt, etc.), peer 120B can increment a nonce value until a hash is generated having the desired proof-of-work characteristics, perhaps a number of leading zero bits among other factors.

Once validity block 135 has been properly calculated and/or validated by the peers, it can be sent to other peers 120 in ecosystem 100 so that validity block 135 will be appended to HHBC 130. Thus, validity block 135 becomes part of the chronicled healthcare history of stakeholder 110. Validity block 135 an be considered accepted as part of the HHBC 130 once other peers 120 pickup and integrate it into their own copies of the HHBC 130.

Figure 2:
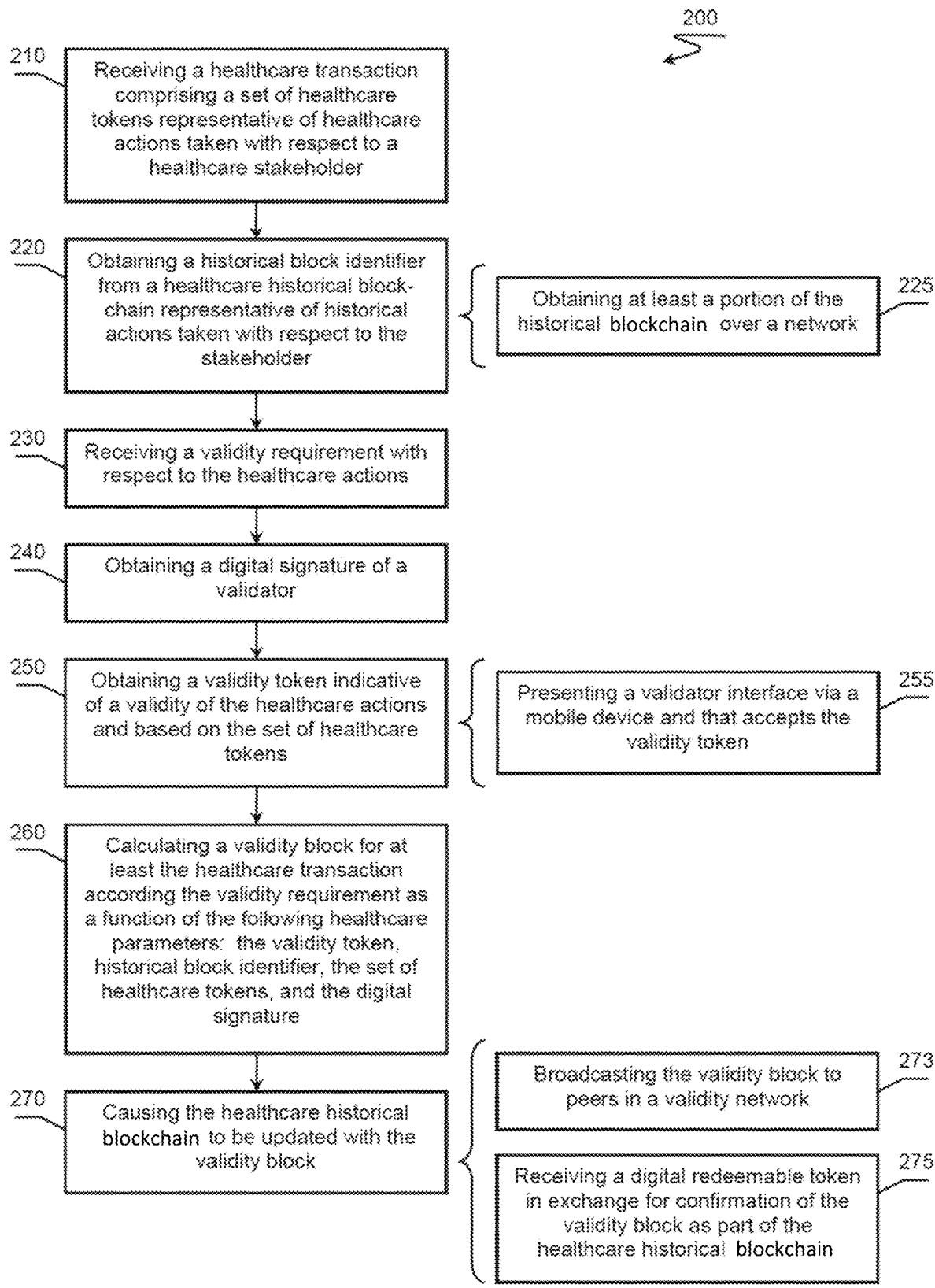
FIG. 2 illustrates a method of validating a healthcare transaction.

FIG. 2 provides a more detailed perspective of method 200 of validating healthcare transactions. Method 200 details the steps of providing validation information with respect to a healthcare transaction represented by healthcare tokens and a validity token among other items. The steps of method 200 are executed by one or more validation devices (e.g., computer clients, computer servers, web servers, mobile devices, clouds service servers, etc.). The validation devices are considered part of healthcare transaction ecosystem. For example, all the devices could be subscribers to a clinical operating system and electronic medical record exchange ecosystem. Although the following steps are described from the perspective of a single validation device, it should be appreciated that multiple devices could be operating together to fulfill the roles or responsibilities described by the steps.

Step 210 includes receiving a healthcare transaction comprising a set of healthcare tokens representative of healthcare actions taken with respect to a healthcare stakeholder. The healthcare tokens can be received over a network, via a web service, through an API call, or other techniques through which data can be exchanged. For example, in a peer-to-peer network, the validation device can receive a broadcast from a peer device where the broadcast comprises serialized healthcare tokens, perhaps in a JSON, XML, or YAML format. The healthcare tokens can represent the inputs or outputs of a healthcare transaction between a stakeholder (e.g., a patient) and another entity (e.g., doctor, insurance company, pharmacy, etc.). Example healthcare tokens could include a test result, a genetic sequence, a diagnosis, a prognosis, a patient identifier, a caregiver identifier, a fee, a payer identifier, or other type of information. More preferred healthcare tokens comprises standardized codes so that all peers can reference healthcare transactions in a uniform manner. Example standardized codes that could be leveraged with the disclosed system include ICD codes, CPT codes, DSM codes, or other known coding standards or those yet to be defined.

Step 220 comprises the validation device obtaining a historical block identifier from a healthcare historical blockchain representative of historical actions taken with respect to the stakeholder. The historical block identifier preferably represents a link to the stakeholder's HHBC. The historical block identifier could comprise a hash value of a previous block header in the HHBC, possibly the last block added to the HHBC. Such an approach is considered advantageous because the hash value incorporates all previously processed blocks, which mitigates the risk of fraud by participants that seek to inject erroneous information to the HHBC. In such cases the block identifier represents a link of continuity across all blocks in the chain.

In view that the validation devices could exist within a peer-to-peer network, a validation device could obtain at least a portion of the HHBC over network as suggested by step 225. Consider a scenario where a new device has subscribed to the ecosystem or is integrated into a cOS environment. Part of the process could include downloading relevant HHBCs, subject to permissions or authorizations, from other peers in the ecosystem. Alternatively, the new peer could download the HHBC or portions thereof directly from a central database.

In some scenarios, an HHBC might not yet exist. For example, a newly born baby might require creation of a new HHBC, or stakeholders that newly engage with the ecosystem might require creation of a new HHBC. With reference to the birth of a baby, the method could include the step of creating the HHBC (not shown) from the set of healthcare tokens. In such a case, the healthcare tokens could comprise a birth token, where the genesis block from the newly created HHBC depends on the birth token or other information relating to the birth. Additionally, the newly created HHBC could depend on one or more parent tokens in the set of healthcare tokens. The parent tokens might represent identifiers that uniquely identify the parents of the baby (e.g., social security number, GUID, private or public key, etc.). This approach is considered advantageous because it allows for linking one HHBC of a stakeholder to the origin of another HHBC.

Step 230 includes receiving a validity requirement with respect to the healthcare actions. The validity requirement can take on many different forms depending on the nature of the healthcare actions or how difficult the validation is intended to be. The validity requirement could be packaged with the healthcare tokens as discussed previously. Alternatively, the validity requirements could be obtained via a validation pool manager or a central authority service.

The validity requirement can provide a proof-of-work difficulty such as requiring a number of leading zero bits in a hash value generated based on the transaction information. Further, the validity requirement can also include factors beyond proof-of-work. For example, the validity requirement could also include two or more factors that depend on a value of a corresponding validity token. In such cases, the validity token could represent an "agreement" with the transaction or a "disagreement" with the transaction, which could then determine the nature of the validity requirement. If the validator "agrees" with the transaction, then the validity requirement might have a low threshold proof-of-work requirements, while a "disagreement" might require a higher threshold proof-of-work requirement. Thus, the disclosed systems could include asymmetric validity requirements depending on the validity tokens. Still further, the validity requirement might also require presence of additional healthcare tokens should the validity token take on different values. Should the validator disagree, the validator might be required to provide recommendations or suggestions on how to alter or correct the healthcare transaction.

The validity requirement can be considered to comprise rules or criteria that must be satisfied before the validation device is considered to have completed its work in processing a block of transactions. In some embodiments, the validity requirements can be described within a package data structure or a protocol packet having a difficulty code. In other embodiments, the validity requirement could include executable code, which can include software instructions (e.g., hash algorithms, analysis techniques, expert system rules, etc.) or algorithms that should be applied to the healthcare transactions.

Step 240 continues by obtaining a digital signature of a validator. The validator can be considered the entity that processes the healthcare tokens to determine if the healthcare transaction should be perceived as being valid or invalid. The digital signature represents a code indicative of the identity of the validator. Although the digital signature could be secured to protect the identity of the validator, there is no requirement that the digital signature be secured. Example digital signatures could include a public key, a private key, an address of the validator peer (e.g., hash-based address, a transaction address, IPv4 address, IPv6 address, GUID, UUID, etc.), or other type of information that identifies the validator. More preferred validator digital signatures exist within a common signature space; peer network addresses for example.

The validator could comprise a human observer or mechanical turk worker that reviews the content of the healthcare tokens. In other embodiments, the validator could comprise an expert system employing one or more rules sets by which the healthcare tokens should be processed. The expert system executing on one peer validation device can be separately or independently programmed from other peers in the network. Such an approach is considered useful because it is expected that a large number of peers will be able process the healthcare tokens from many different perspectives according to their individual rules. For example, the ecosystem could employ one or more kernel functions by which the expert systems evaluate the healthcare tokens for validity. The kernel functions can be distributed across the peers and separately evaluated. Alternatively, the expert systems could employ trained machine learning algorithms (e.g., neural networks, support vector machines, etc.) that have been trained on separate or disparate data sets. This is considered advantageous because it ensures the peers have different, learned perspectives on the subject matter, which mitigates the risk of all peers possibly generating false negatives or false positive results if they are trained exactly on the same data.

Step 250 includes the validation device obtaining a validity token indicative of the validity of the healthcare actions and based on the set of healthcare tokens. The validity token could be obtained as a code from a validity analysis routine where the code could take on binary value (e.g., valid-invalid; agree-disagree, 0-1, etc.), or could take on a range of values. For example, if an expert system is operating as a validator, the validity token could be a score between −1.0 (invalid) and 1.0 (valid), for example, indicating a confidence score with respect to the validity decision; the confidence score could also be between 0 and 10 as another example.

In other embodiments, the validity token can be obtained via validator interface. Step 255 suggests the method could further include presenting the validator interface via mobile device where the interface accepts a user selected validity token. As an example, consider a scenario where a hospital has subscribed to the disclosed ecosystem. Each subject matter expert (e.g., surgeons, pediatricians, gastroenterologists, oncologists, etc.) could be provisioned with a tablet computer configured to operate as the validation device or as the validator interface. As healthcare transactions are taking place within the hospital, the corresponding healthcare tokens can be routed to the appropriate subject matter experts. The tablet displays the necessary healthcare tokens or healthcare transaction information and requests input from the subject matter expert with respect to the validity of the transaction. The tablet could present a list of validity options to the expert who then selects one or more of the options.

Upon establishing one or more validity tokens representing the opinion of the healthcare transaction, the method continues at step 260 by calculating or otherwise generating a validity block for one or more healthcare transactions according to the validity requirement and as a function of the validity token, historical block identifier, the set of healthcare tokens, the digital signature, or other parameters relevant to the healthcare transactions. Calculating the validity block is consider to comprises generation of a value that depends on the history of the HHBC as well as the current transactions being processed. More specifically, the generated value also depends on the validity token. For example, the function could be a hash function (e.g., SHA, Scrypt, MD5, RIPEMD, WHIRLPOOL, etc.) applied to the concatenation of the various pieces of information in the healthcare transactions, which is then hashed with the validity block's header information. It should be appreciated that step 260 could be iteratively applied until the validity block takes on characteristics that satisfy the validity requirements. For example, in the cases of applying a hash to the healthcare parameters, the hash can also be applied to a nonce and a time-stamp preferably bound within the validity block's header. If the resulting value fails to satisfy the validity requirements, the nonce can be incremented or the time-stamp could be updated and step 260 can be repeated based on the new value.

The resulting validity block comprises more than just the resulting hash value. It also includes the various information elements that gave rise to the hash value. Thus, the validity block represents a chronicle or ledger of the healthcare transactions. Such an approach is advantageous as it ensures the validity block retains a link to other blocks in the HHBC as well as provides a searchable or analyzable data object. Additionally, by providing the information other peers in the network, the peer can validate the proof-of-work.

Figure 3:
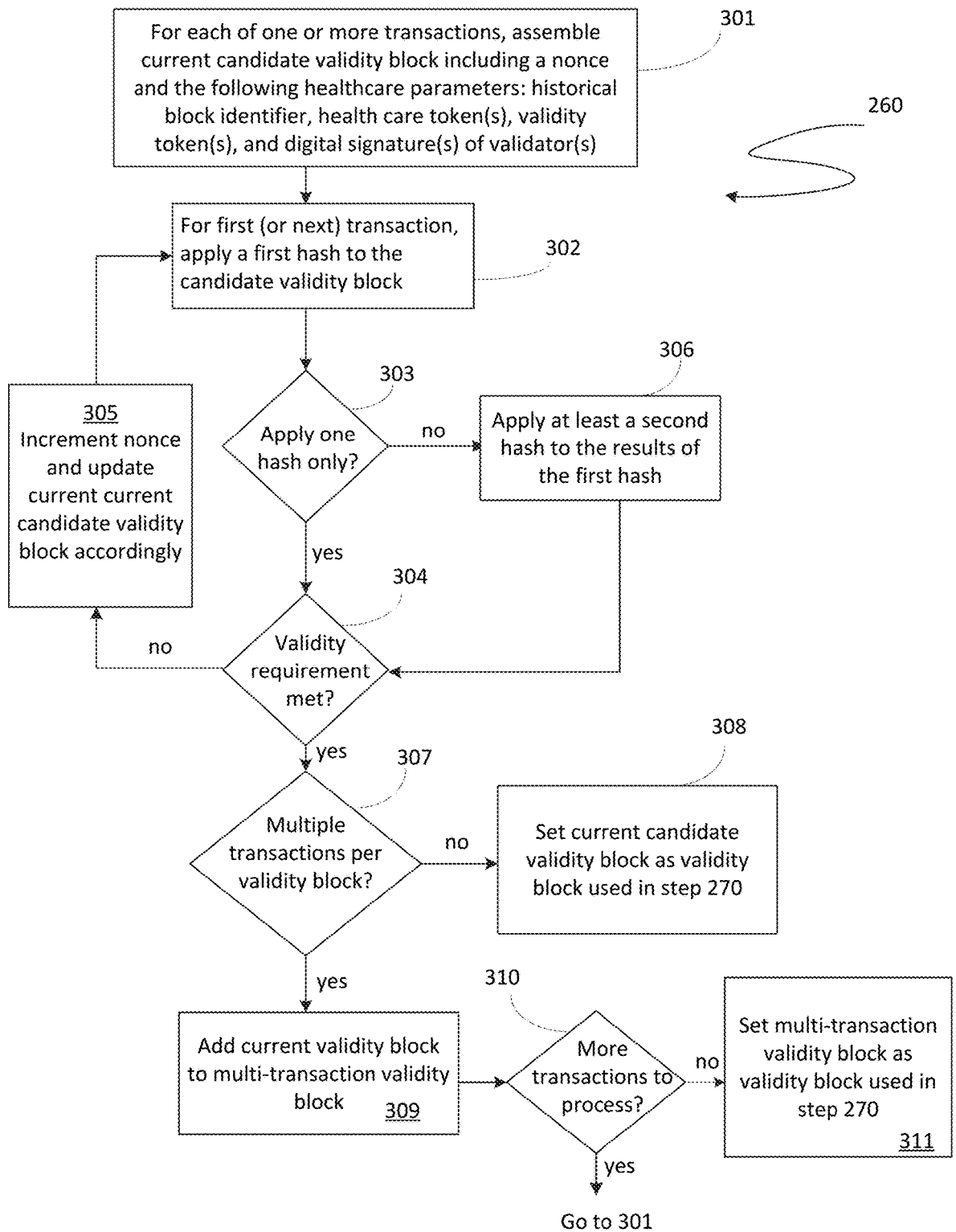
FIG. 3 illustrates further details of processing carried out by one of the steps of FIG. 2.

FIG. 3 is a flow diagram showing processing steps carried out, in one embodiment, by step 260 of FIG. 2. As will be described further, the disclosed process allows the flexibility to generate validity blocks including one transaction per block or including multiple transactions per block. This flexibility recognizes that, in the healthcare context, in some instances, it might be useful and efficient to process multiple transactions for a single validity block, whereas in other contexts, it might be more useful to process a single transaction. As one example, a patient visit might generate multiple transactions for that patient or might only generate a single transaction for that patient. In the former case, processing all transactions together can be efficient and also provide a basis for linking multiple transactions for a patient to a single visit, thereby providing visit information without necessarily requiring a separate "visit" field in a data structure stored in the HHBC. In the latter case, especially if the patient is not expected to generate additional transactions for a significant time period, it might be useful to process validation of the single transaction and generate a validity block to be added to the HHBC for that patient without waiting for additional transactions to accrue. In another example, as previously mentioned, a doctor or other healthcare provider might be associated with many transactions per day and, therefore, it might be more efficient to generate a validity block each day including multiple transactions to be added to that stakeholder's HHBC.

Referring now in detail to FIG. 3, step 301 assembles a candidate validity block including a nonce and the following healthcare parameters: a historical block identifier, one or more healthcare tokens, one or more validity tokens (generated based on a validator reviewing the healthcare tokens), and one or more digital signatures associated with a validator generating the validity tokens. Step 302 applies a first hash to the candidate validity block. Step 303 determines whether the process should only use one hash. If no, then step 306 applies at least a second hash to the result of the first hash before proceeding to step 304. Step 306 allows the method to, if desired, increase the processing required to achieve proof-of-work. If the result of 304 is yes, then the method proceeds directly to step 304. Step 304 determines whether the result of step 302 (if only one hash applied) or step 306 (if multiple hashes applied) has met the validity requirement. One example of a typical proof-of-work validity requirement in this context is that the hash result has a certain number of leading zeros. However, many variations are possible. If the result of step 304 is no, then step 305 increments the nonce in the current candidate validity block and processing returns to step 302 to recalculate a hash using the new nonce value.

If the result of step 304 is yes, then step 307 determines whether multiple transactions will be added to a single validity block. If the result of step 307 is no, then step 308 sets the current validity block as the validity block provided for step 270 of FIG. 2. If the result of step 307 is yes, then step 309 adds the current validity block to a multi-transaction validity block and step 310 determines whether there are more transactions to process for the multi-transaction validity block. If yes, then the method returns to step 301 to process another transaction. If the result of step 310 is no, then step 311 sets the current multi-transaction validity block as the validity block to be used by step 270 of FIG. 2.

A multi-transaction validity block could be constructed in a variety of ways. In the illustrated example, one or more hash functions are applied to the data for each transaction individually to meet the proof-of-work or other proof requirement (e.g., identifying a nonce that yields the required result), and then multiple validity blocks are concatenated together to form a multiple transaction validity block prior to broadcasting the validity block to peers on the network. However, in another example, multiple proposed validity blocks could be concatenated together prior to applying the hash function. In this scenario, the proof-of-work is carried out for multiple transactions together.

Other scenarios are possible. For example, the hashes of each transaction be can concatenated together to arrive at the final hash value for the transactions which can then be concatenated with the information from the validity block header to arrive at the final hash value. It is not required to repeatedly recalculate hashes of all transactions in such cases. Rather the transactions can be organized according to a Merkle tree, which reduces how often hashes of the transactions in the tree require recalculation.

Returning to FIG. 2, the method continues at step 270 by the validation device causing the HHBC to be updated with the validity block. For example, the newly completed validity block can be appended to the chain in time stamp order. In peer-to-peer environments, the validation device could broadcast the validity block to peers in the validity network as suggested by step 273. Each of the peers can then append the validity block to a locally stored version of the HHBC. Should multiple peers generate completed validity block for the transactions, then the validity blocks forming the longest chain could be adopted as the foundation for future calculations and could represent confirmation of the block.

In view that each of the peers is performing work to render a validity opinion on a transactions, it is possible for the peer to receive compensation for the work. Step 275 could include the validation device receiving a digital redeemable token in exchange for integration of the validity block as part of the HHBC. The digital token could be virtual currency (e.g., a digital coin, BitCoin, Litecoin, Peercoin, Dogecoin, a propriety healthcare coin, etc.), a fiat currency, a coupon, an increase in accreditation score, or even an exchanged service.

The disclosed system and methods describe an HHBC for each entity where the HHBC can include information regarding an opinion regarding validity of such transactions. The disclosed systems can also leverage additional features or capabilities that enhance the value of the techniques.

In the embodiment illustrated in FIGS. 1-3, a validator reviews the health care transactions to confirm that the data makes sense, issues a corresponding validity token, and then a peer in the network puts forth processing effort to validate the blocks via proof-of-work or other proof, and circulates a validity block for the transaction, the validity block being for appending to the HHBC of a corresponding stakeholder. However, as previously discussed, other types of proof-of-work can be used, or, instead of using proof-of-work, proof-of-stake or other methods could be used for arriving at an appropriate validity block. In cryptocurrencies, proof-of-stake represents currency that is put up as collateral when mining or validating blocks for coins. In the healthcare context, the proof of stake could include evidence of insurance, a monetary cost, an accreditation score, or other value that is indicative of value to the validator. This approach is considered advantageous on the ground that proof of stake requires less computing resources than proof of work. Still other types of proof that could be leveraged with the disclosed subject matter include proof of trust where others indicate the perceived value of the validators opinion; or proof of evidence where the validator provide evidence on how often they are right with their validation or how often they conform to other validator's opinions. In one alternative, a trusted peer or central authenticator computer can simply confirm that the digital signature or digital signatures associated with the validity tokens belongs to a trusted reviewer, assemble an appropriate validity block, and circulate for appending to the appropriate HHBC. In another example, an entity demonstrates a stake in the transaction, through payment or otherwise, and then generates validity blocks accordingly, perhaps including an appropriate digital signature of the entity generating the validity block.

The HHBC essentially represents a healthcare path taken by a patient through their entire life. Each block in the chain can be reviewed, possibly via a browser, to analyze the path taken by the patient. Each patient can be analyzed individually or collectively for longitudinal studies. Such approaches would be of high value with respect to patients that have been prescribed similar, if not the same, drugs. The healthcare transactions after the prescription is fulfilled can be analyzed to establish correlations of healthcare outcomes across patient populations.

The disclosed approach could be considered semi-secure in the sense that private information can be encoded within various keys. Still, explicit security can be applied to further secure the HHBC by encrypting the HHBC. Once a peer has established its identity, it can be granted a key to decrypt the HHBC information as needed.

The HHBCs are dynamic, living objects that evolve over time by adding validity blocks in response to healthcare interactions. In some embodiments, the nature of the evolution of the HHBC can be analyzed to derive one or more trends. For example, the rate of change in the HHBC (e.g., transactions per month) could be a leading indicator of health issues. Further, such information could be correlated with external factors (e.g., environmental conditions, etc.) across stakeholder populations.

Although the disclosed approach relates to healthcare, it should be appreciated that the techniques can also be adapted for other markets beyond healthcare. Such an approach is useful to ensure that those providing service do not take advantage of the stakeholders. Example markets that could leverage such validity information would include the mortgage industry to reduce predatory loans, automotive repairs to reduce unjustified repairs, employee evaluations to ensure those in power are accountable for decisions, credit card expenditures, financial transactions, or other markets.

Yet another interesting aspect of the disclosed subject matter is that each validity block in the blockchain includes data representing each healthcare transaction, which could be read by a browser as discussed above. Such healthcare data can take on a broad spectrum of information beyond the time stamps or tokens discussed previously. In addition, each transaction can comprise pointers to EMRs or genomic data that were used within respect to the transactions. The pointers could include human readable pointers, perhaps a file names, file handles, URLs, URIs, or other type of text-based address. In some scenarios, the pointers could comprise document object identifiers (DOIs; see URL www-.doi.org), which point to documents. More preferred pointers represent pointers to permanent references that index to supporting evidence, documents, EMRs, or other types of documents throughout time. In some embodiments, the pointers reference an indexing system, which then resolves the pointer address to the actual location for such documents. The advantage of such an approach is that the documents can be moved from one storage location to another as large amounts of time passes. Through inclusion of document pointers, the HHBC is able to link with EMR systems without requiring supporting a specific or proprietary EMR implementation. The pointers could be a priori encrypted according to the stakeholder's key to further secure the information. Should a current or future analyst need access to such documents, they can request authorization from a central authority or from the stakeholder. Thus, the inventive subject matter is considered to include a HHBC Name Service (HNS) that can resolve HHBC pointers or address to specific network locations. This approach is considered advantageous because it allows for indirect referencing of information from one block or blockchain to another regardless of where the actual data is stored. In distributed systems implemented on torrent protocols, the pointers or addresses of a block could conform to the same address space as used by the computers storing the data.

It should be appreciated that the disclosed approaches allow for analysis of transactions related to clinical or evidence content in an agnostic manner. In view that transactions in the HHBC have document pointers that leverage standardized addresses, there is no requirement that the validation devices understand the formats used to store the clinical data or evidence data. Still, in some embodiments, the validation devices can be configured with application-specific agents or adapters that are able to incorporate the clinical or evidence data in to validity or transaction processing according to the data's respective formats if desired. For example, the validator could request access to supporting clinical or evidence data. Once authorized, the validation device can obtain the requested data and use a local adapter to convert, if necessary, the data from its format to a presentation format (e.g., HTML5, Flash, etc.) that is consumable by the validator (e.g., a doctor, a nurse, etc.).

The validity token can also take on interesting aspects with respect to the inventive subject matter. The examples presented above assume that a peer is operating as a validator of one or more healthcare transaction. It is also possible for the peer to operate as a transaction processing device that obtains the validity token from other validators. Reference back to FIG. 1, peer 120B might process the healthcare transaction from peer 120A while also receiving a corresponding validity token from peer 120D. Peer 120D generates the validity token after receiving the necessary healthcare tokens or references to supporting clinical evidence to render the validity opinion. Such an approach is considered as advantageous because multiple entities, possibly non-affiliated entities, participate in the processing of the healthcare transactions, which further mitigates the risk of fraud.

Yet another variant of the disclosed technology could include embodiments that comprise one or more automated veto schemes that operate according to various modes. In some embodiments, the validation device could veto the current healthcare transaction, which would force the healthcare transaction participants to re-evaluate an in-process transaction. Such an approach is useful to pre-adjudicate insurance claims associated with the healthcare transaction. In other embodiments, once the validation device completes its construction of the validity block and submits the block to the peers, the peers could then attempt to verify the validity block from a processing perspective or from a validity perspective. If sufficient peers fail to verify the validity block, perhaps based a vote, the validity block can be vetoed. This approach provides for further peer review and enforcement of treatment care standards.

The disclosed techniques centered on the HHBC also give rise to interesting capabilities with respect to the Internet-of-Things (IOT). Clinical evidences generated from devices or services can be routed to preferred medical data custodians, which can permit access to the data upon proper authentication or authorization. Transactions within the HHBC blocks can then reference such clinical data via corresponding pointers referencing the designated medical data custodian site(s). This approach allows the HHBCs to reference data generated across the broad healthcare lifecycle care including data from the IOT (e.g., sensors, personal area networks, ambient data, etc.), primary care stakeholders (e.g., PCP, etc.), second care stakeholders (e.g., specialists, etc.), tertiary care stakeholders (e.g., hospitals, insurance companies, etc.), quaternary care stakeholders (e.g., post-hospitalization, hospice, etc.) no matter the model of care. The models of care (e.g., self-care, retail care, remote care, etc.) are therefore able to drive evidence-based data to the medical data custodians while providing access to the data for analysis through HHBCs.

In some embodiments, behavior analytics information as evidenced by HHBC information can be supplied to various market places (e.g., Amazon, Google, etc.). The market places would leverage such personal or demographic information to enable service providers to deliver highly targeted healthcare content to consumers, subject to privacy constraints. For example, medical data custodians can generate one or more healthcare campaigns that are triggered based on features of HHBCs or corresponding behavior metrics. When a consumer interacts with the market places (e.g., purchases products, searches for services, etc.), campaigns can be delivered to the consumer where the campaigns. Such campaigns can be constructed to have attributes or parameters having values that satisfy matching criteria with respect to the consumer's behaviors or their known healthcare transactions as well with respect to the nature of the consumer's interactions with the market place (e.g., non-healthcare related activities, personal preferences, intents, personas, etc.).

The medical data custodians can also use HHBCs as a foundation for offering for-fee data services. The custodians can offer access to the HHBCs in a secure, confidential fashion to one or more analyst entities (e.g., researchers, insurance companies, hospitals, etc.). For example, an insurance company could pay for access to a collection of HHBCs filtered based on demographics, location, time, or other factors. The insurance company could then apply actuarial algorithms to build risk tables. For such an analysis, the insurance company does not necessarily require patient identification or other private information. Rather, such an analysis could only use sanitized data.

The custodians can charge entities for accessing the HHBCs based on many factors, possibly including number of HHBCs accessed, granularity of transactions information, nature of the data, length of time accessed, or other aspects. As an example, consider a scenario where a pharmaceutical company wishes to conduct a longitudinal study on one of their products in the field. The company can purchase rights to access all HHBCs that having transactions that include references to their products as well as a control group having HHBCs of a similar nature but lacking references to the company's products. The data custodian can grant access to the HHBCs in exchange for a fee while also restricting access private information (e.g., patient names, addresses, phone numbers, etc.) thereby allowing the pharmaceutical company to conduct their desired analysis. Perhaps, the company can filter the HHBCs into demographic groups or age ranges, and attempt to establish correlations between point of prescription and outcomes. The medical data custodian could charge the company based on the level of access according to one or more fee schedules. In some embodiments, the company might be a peer in the HHBC ecosystem and might have copies of the HHBCs. However, they might not be authorized for reviewing the data. In such a case, the medical data custodian could charge the company for a temporary key that unlocks the data within the HHBCs.

Figure 4:
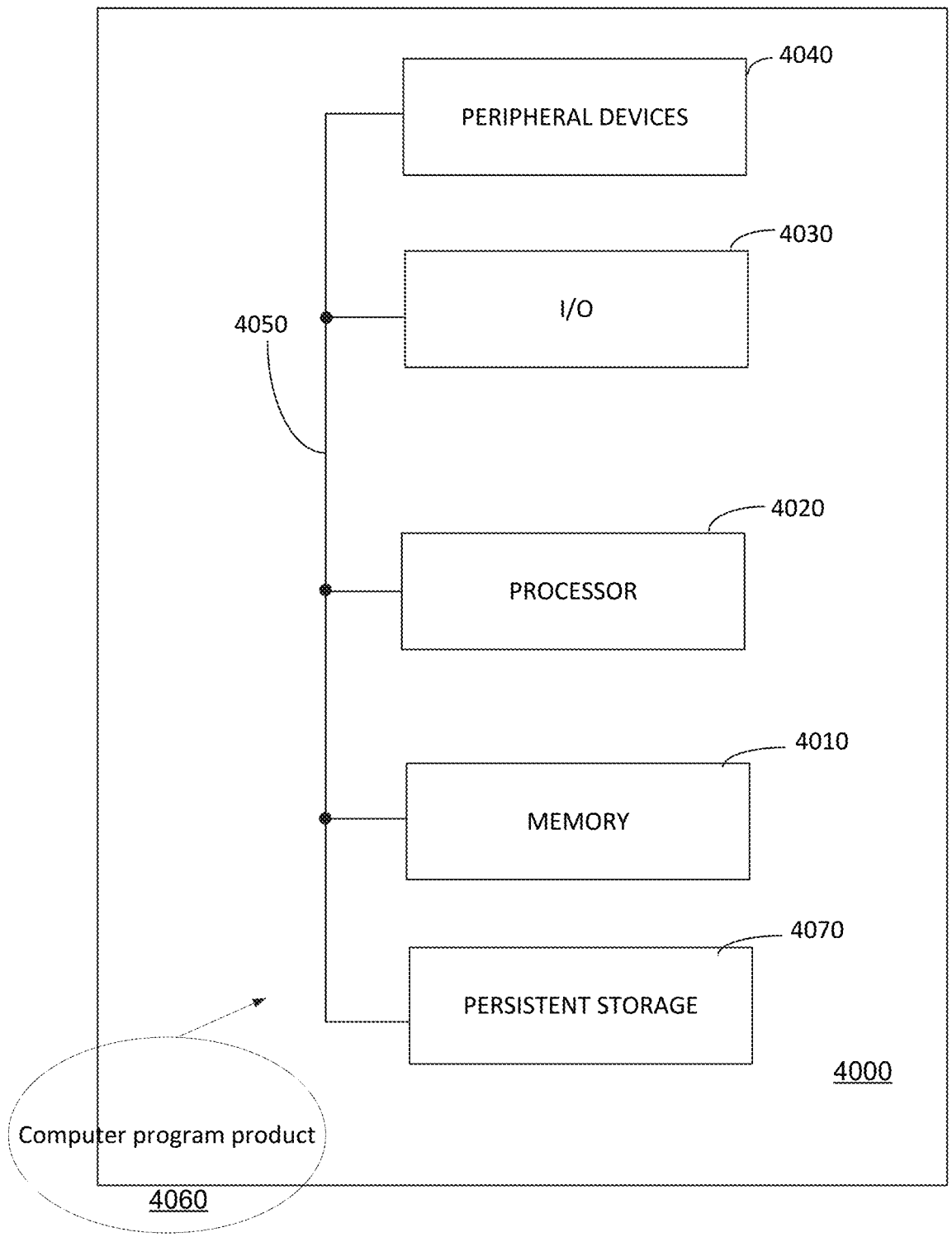
FIG. 4 shows an example of a computer system (one or more of which may provide the components shown in FIG. 1) that may be used to execute instruction code contained in a computer program product in accordance with an embodiment of the present invention.

FIG. 4 shows an example of a computer system 4000 (one or more of which may provide the components of FIG. 1) that may be used to execute instruction code contained in a computer program product 4060 in accordance with an embodiment of the present invention. Computer program product 4060 comprises executable code in an electronically readable medium that may instruct one or more computers such as computer system 4000 to perform processing that accomplishes the exemplary method steps performed by the embodiments referenced herein. The electronically readable medium may be any non-transitory medium that stores information electronically and may be accessed locally or remotely, for example via a network connection. The medium may include a plurality of geographically dispersed media each configured to store different parts of the executable code at different locations and/or at different times. The executable instruction code in an electronically readable medium directs the illustrated computer system 4000 to carry out various exemplary tasks described herein. The executable code for directing the carrying out of tasks described herein would be typically realized in software. However, it will be appreciated by those skilled in the art, that computers or other electronic devices might utilize code realized in hardware to perform many or all of the identified tasks without departing from the present invention. Those skilled in the art will understand that many variations on executable code may be found that implement exemplary methods within the spirit and the scope of the present invention.

The code or a copy of the code contained in computer program product 4060 may reside in one or more storage persistent media (not separately shown) communicatively coupled to system 4000 for loading and storage in persistent storage device 4070 and/or memory 4010 for execution by processor 4020. Computer system 4000 also includes I/O subsystem 4030 and peripheral devices 4040. I/O subsystem 4030, peripheral devices 4040, processor 4020, memory 4010, and persistent storage device 4060 are coupled via bus 4050. Like persistent storage device 4070 and any other persistent storage that might contain computer program product 4060, memory 4010 is a non-transitory media (even if implemented as a typical volatile computer memory device). Moreover, those skilled in the art will appreciate that in addition to storing computer program product 4060 for carrying out processing described herein, memory 4010 and/or persistent storage device 4060 may be configured to store the various data elements referenced and illustrated herein.

Those skilled in the art will appreciate computer system 4000 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An indexed storage system comprising:
    at least one non-transitory computer readable memory storing software instructions and a ledger of linked transaction blocks storing transaction data wherein the ledger is associated with a stakeholder; and
    at least one processor coupled with the at least one non-transitory computer readable memory to execute one or more software instructions stored in the non-transitory computer readable memory, wherein the processor upon execution of the software instructions:
    receives transaction data associated with a transaction having supporting evidence data in one or more data formats;
    obtains a pointer, wherein the pointer references an indexing system, the pointer pointing to a block of data comprising the supporting evidence data;
    locates, based on the pointer, the supporting evidence data at the specified network location;
    generates a validity token based on the supporting evidence data, wherein the validity token represents a validity analysis;
    adjusts a validity proof requirement based on the validity analysis represented by the validity token; and
    causes at least one of the linked transaction blocks in the ledger to be updated with at least the pointer and transaction data after a validation that includes meeting the adjusted validity proof requirement,
    wherein the pointer conforms to an address space used by a plurality of distributed nodes across a computer network operable for storing the supporting evidence data independent of the one or more data formats.

2. The system of claim 1, wherein the ledger comprise at least one of the following types of ledgers: a public ledger, a private ledger, a protected ledger.

3. The system of claim 1, wherein the ledger comprises a blockchain.

4. The system of claim 1, wherein the ledger comprises a distributed ledger.

5. The system of claim 1, wherein the ledger comprises a healthcare ledger.

6. The system of claim 5, wherein the transaction blocks comprise healthcare transactions.

7. The system of claim 1, wherein the address space conforms to a torrent protocol.

8. The system of claim 1, wherein the pointer comprises at least one of the following: a file name, a file handle, a URL, a URI, a DOI, an encrypted pointer, and a network location.

9. The system of claim 1, where in the validation comprises a voting among peers.

10. The system of claim 9, wherein the voting among peers comprises voting among validators.

11. The system of claim 1, wherein the at least one processor, further receives a digital token upon successful validation.

12. The system of claim 11, wherein the digital token comprises at least one of the following: a virtual currency, a coupon, a score, and an exchange service.

13. The system of claim 1, wherein the validity proof requirement comprises a proof-of-work.

14. The system of claim 1, wherein the proof requirement comprises a proof-of-stake.

15. The system of claim 1, wherein the proof requirement comprises a proof-of-evidence.

16. The system of claim 1, wherein the pointer points toward a data custodian computer storing the evidence data.

17. The system of claim 16, wherein the data custodian computer operates as a for-fee data service.

18. The system of claim 1, further comprising a computing device operating as a name service that resolves the pointer toward a specific network location.

19. The system of claim 1, wherein the evidence data comprises at least one of the following: a document, an electronic medical record, sensor data, ambient data, medical data, and behavior analytics.

20. A method of storing indexed information, the method comprising:
    receiving transaction data associated with a transaction having supporting evidence data in one or more data formats;
    obtaining at least one pointer, wherein the pointer references an indexing system, the pointer pointing to at least one block of data comprising the supporting evidence data;
    locating, based on the pointer, the supporting evidence data stored a specified network location;
    generating a validity token based on the supporting evidence data, wherein the validity token represents a validity analysis;
    adjusts a validity proof requirement based on the validity analysis represented b the validity token;
    validating the transaction, wherein the transaction validation includes meeting the adjusted validity proof requirement; and
    updating at least one linked transaction block in a ledger comprising one or more linked transaction blocks wherein the ledger is associated with a stakeholder and the at least one linked transaction block is updated with the at least one pointer and the transaction data, and the at least one pointer conforms to an address space used by a plurality of distributed nodes across a computer network operable for storing the supporting evidence data of the validated transaction independent of the one or more data formats.

21. A computer program product comprising instructions stored in a non-transitory machine-readable medium, the instructions including instructions which when executed by a processor, cause the processor to perform:
    receiving transaction data associated with a transaction having supporting evidence data in one or more data formats;
    obtaining at least one pointer, wherein the pointer references an indexing system, the pointer pointing to at least one block of data comprising the supporting evidence data;
    locating, based on the pointer, the supporting evidence data stored at a specified network location;
    generating a validity token based on the supporting evidence data, wherein the validity token represents a validity analysis;
    adjusting a validity proof requirement based on the validity analysis represented by the validity token;
    validating the transaction, wherein the transaction validation includes meeting the adjusted validity proof requirement; and updating at least one linked transaction block in a ledger associated with a stakeholder comprising one or more linked transaction blocks wherein the at least one linked transaction block is updated with the at least one pointer and the transaction data, and the at least one pointer conforms to an address space used by a plurality of distributed nodes across a computer network operable for storing the supporting evidence data of the validated transaction independent of the one or more data formats.

* * * * *